May 24, 1966 W. ZOMBORY ETAL Plant Pat. 2,633
DIANTHUS PLANT
Filed April 20, 1965
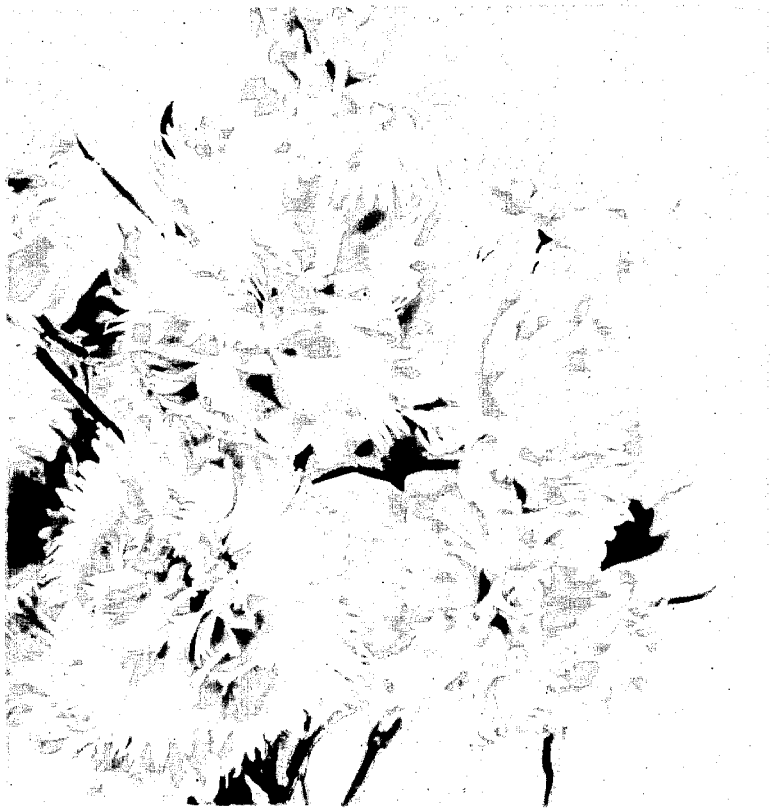
Inventors.
William Zombory and
Sophia B. Zombory
By: Robb & Robb
Attorneys.

United States Patent Office

Plant Pat. 2,633
Patented May 24, 1966

2,633
DIANTHUS PLANT

William Zombory and Sophia B. Zombory, both of Detroit, Mich., assignors to Jackson & Perkins Company, Newark, N.Y., a corporation of New York Filed Apr. 20, 1965, Ser. No. 449,664
1 Claim. (Cl. Plt.—72)

The present invention relates to a new and distinct variety of dianthus plant, which was originated by us by crossing an unnamed and unpatented large pink-flowered variety of the species botanically known as "Dianthus allwoodi" with an unnamed and unpatented white flowered seedling of "Dianthus Caprice" (Plant Patent No. 1,851).

The primary objective of this breeding was to produce a new and improved dianthus variety of an ever-blooming and compact form of the species "Dianthus allwoodi," but which bears flowers of a different color than those of this species. This objective was fully achieved, along with other desirable improvements, as evidenced by the following unique combination of characteristics which distinguish our new variety from its parents, as well as from all other varieties of which we are aware:

(1) A hardy, upright and compact habit of plant growth;

(2) Production of blooms commencing the first year when grown from cuttings;

(3) A continuous blooming habit;

(4) Large flowers having frilled petals, (5) A distinctive and attractive general color tonality of the flowers corresponding to Tyrian Rose, overcast with Spinel Pink; and (6) A sweet Old Spice flower fragrance.

Asexual reproduction of our new variety by cuttings, as performed at Detroit, Michigan, and also at Newark, New York, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Seedling.

*Seed parent.*—An unnamed large pink-flowered variety of the species botanically known as "Dianthus allwoodi."

*Pollen parent.*—An unnamed and unpatented white flowered seedling of "Dianthus Caprice."

Blooming season: Starts blooming the first year when grown from cuttings, with blooms produced during June and July and again during September until frost.

*Plant*

Growth: Tall (about 14 inches); compact; upright.

Leaves: Many bottom leaves in tufts; about 5 inches long; narrow; thick. Color—Lincoln Green, Plate 14, with a silvery sheen of Greenish Glaucous, Plate 41.

Flower stem: About 12 inches long; strong. Color—Light Elm Green, Plate 17.

*Flower*

Borne: From 3 to 5 flowers per stem; borne mostly on own branched stalks, but some of the laterals nearly sessile.

Size: About 2½ inches in diameter.

Petals: From 25 to 30 in number; frilled; about ¾ inch long; about ½ inch wide; small blotch of White, plate 53 at beginning of throat. Color—Upper side—Tyrian Rose, Plate 12, overcast with Spinel Red, Plate 26; reverse side—Spinel Red, Plate 26, overcast with Spinel Pink, Plate 26; claw—White, Plate 53, blended with Glass Green, Plate 31.

Calyx: Cylindrical; small teeth; about ¾ inch long; erect; calyx splits on wide open flower. Color—Ivy Green, Plate 31, with teeth of Varley's Green, Plate 18.

Bracts: 4 in number; small. Color—Light Cress Green, Plate 31, edged with Indian Lake, Plate 26.

Stamens: About 8 in number; some protruding. Color—White, Plate 53.

Anthers: Color—Pale Lobelia Violet, Plate 37.

Ovary: Small; oval.

Fragrance: Sweet Old Spice.

We claim:

A new and distinct variety of dianthus plant, substantially as herein shown and described, characterized particularly as to novelty by the unique combination of a hardy, upright and compact habit of plant growth, production of blooms commencing the first year when grown from cuttings, a continuous blooming habit, large flowers having frilled petals, a distinctive and attractive general color tonality of the flowers corresponding to Tyrian Rose, overcast with Spinel Pink, and a sweet Old Spice flower fragrance.

No references cited.

ABRAHAM G. STONE, *Primary Examiner.*